(12) United States Patent
Stewart

(10) Patent No.: US 7,022,297 B2
(45) Date of Patent: Apr. 4, 2006

(54) METHOD AND SYSTEM FOR PURIFYING OR CLEANSING A GAS STREAM OR GASEOUS BODY

(76) Inventor: Shawn Alan Stewart, 73 Donnelly St., Turfontein, 2190 (ZA)

( * ) Notice: Subject to any disclaimer, the term of this patent is extended or adjusted under 35 U.S.C. 154(b) by 132 days.

(21) Appl. No.: 10/333,794

(22) PCT Filed: Jul. 24, 2001

(86) PCT No.: PCT/IB01/01320

§ 371 (c)(1),
(2), (4) Date: Jul. 18, 2003

(87) PCT Pub. No.: WO02/07860

PCT Pub. Date: Jan. 31, 2002

(65) Prior Publication Data

US 2004/0028586 A1  Feb. 12, 2004

(51) Int. Cl.
*B01D 47/00* (2006.01)
*B01J 8/00* (2006.01)
*C07C 11/24* (2006.01)

(52) U.S. Cl. .............. 423/210; 423/213.5; 423/239.1; 423/245.3

(58) Field of Classification Search ............ 423/210, 423/212, 213.2, 213.5, 235, 239.1, 242.1, 423/244.01, 244.02–244.04, 244.06, 246, 423/247, 215.5, 244.09, 244.1, 245.1, 245.2, 423/245.3
See application file for complete search history.

(56) References Cited

U.S. PATENT DOCUMENTS 3,911,080 A * 10/1975 Mehl et al. ................ 423/210
4,107,268 A * 8/1978 O'Neill et al. ............. 423/210
4,443,342 A * 4/1984 Stas et al. .................. 210/759
4,455,287 A * 6/1984 Primack et al. .......... 423/576.6
4,574,076 A * 3/1986 Castrantas .................. 423/224
4,595,577 A * 6/1986 Stas et al. ................ 423/245.2
5,468,628 A * 11/1995 Aust et al. .................. 435/168

(Continued)

FOREIGN PATENT DOCUMENTS

EP          0213628      * 3/1987
EP          0 620 037      10/1994

(Continued)

OTHER PUBLICATIONS

"Superoxide dismutase", http://en.wikipedia.org/wiki/Superoxide_dismutase, foudn and viewed Mar. 24, 2005, 2 pages.*

(Continued)

*Primary Examiner*—Colleen P. Cooke
(74) *Attorney, Agent, or Firm*—Jeffrey Costellia; Nixon Peabody LLP

(57) ABSTRACT

A method and system for eliminating, in whole or in part, contaminants in a gas stream or gaseous body such as air or an exhaust gas or gas emission stream is provided. The method includes the steps of contacting the gas stream or gaseous body with a biocide containing liquid so as to eliminate, in whole or in part, the contaminant(s). The biocide containing liquid is typically an aqueous solution, suspension, or emulsion comprising hydrogen peroxide ($H_2O_2$) in combination with a catalyst for enhancing the activity thereof, the catalyst preferably comprising a superoxidedismutase formed from the combination of elemental copper (Cu), silver (Ag), manganese (Mn) and zinc (Zn). The method and system find particular application in the combating of sick building syndrome (SBI) and building related illness (BRI).

11 Claims, 1 Drawing Sheet

U.S. PATENT DOCUMENTS 5,527,517 A * 6/1996 Bridges et al. ............. 423/210
6,716,808 B1 * 4/2004 Rohrbaugh et al. ......... 510/507

FOREIGN PATENT DOCUMENTS

GB       1 456 057      11/1976
WO     WO 88 10122      12/1988

OTHER PUBLICATIONS

"SuperOxideDismutase", http://cam.ucsd.edu/~mholst/biophysics/sod0.html, found and viewed Mar. 24, 2005, 1 page.*

"Mining Ind. Safety Res. Inst." Feb. 7, 1993; Abstract.

* cited by examiner

METHOD AND SYSTEM FOR PURIFYING OR CLEANSING A GAS STREAM OR GASEOUS BODY

BACKGROUND OF THE INVENTION

THIS invention relates to a method and system for purifying or cleansing a gas stream or gaseous body containing one or more contaminants.

It is well established that outdoor air pollution can cause serious human illness. Air pollution can cause burning eyes and noses, itchy irritated throats as well as breathing difficulties. Some chemicals can cause cancer, birth defects, brain and nerve damage, long-term injury to lungs and even premature death. As a result, protection of the public health is a driving force behind the laws and regulations that are being, and have been, put into place to clean up the environment. However, ridding outdoor air toxic contaminants has often overlooked indoor air quality (IAQ).

The results of numerous scientific investigations have revealed many reported outbreaks of what is known as Sick Building Syndrome (SBS) and Building Related Illness (BRI) as a direct result of indoor air pollution (IAP) in office and other public access buildings.

SBS is used to describe the situation in which building occupants experience acute health and comfort defects that are linked to time spent in the building. BRI is the term used when diagnosable illness and symptoms are identified and directly attributed to airborne building material contaminants.

In modern society, it is believed that most people spend as much as 90% of their time indoors. The US Environmental Protection Agency (EPA) has indicated that IAP may be between 2–5 times higher than accepted levels, and up to 100 times higher than outdoor pollution levels.

The World Health Organisation (WHO) Committee Report on IAQ suggested that 30% of new and re-modelled buildings globally are subject to excessive complaints of IAQ and have unusually high rates of SBS and/or BRI. For example, according to the SA Singapore embassy, 92% of all absenteeism in Singapore can be attributed to SBS and/or BRI.

IAQ is rated within the top 5 of the US EPA's most critical global concerns alongside ozone depletion, global warming and the like. It has been reported, for instance, that in 1989, the US economy suffered a staggering US $65 bn loss due to SBS and BRI. The absenteeism levels, due to poor health caused by IAP, resulted In this huge productivity decrease.

SUMMARY OF THE INVENTION

According to the invention, a method of purifying or cleansing a stream of gas or gaseous body containing one or more contaminants, in particular air or an exhaust gas stream, includes the steps of contacting the gas stream or gaseous body with a biocide containing liquid so as to eliminate, in whole or in part, the contaminant(s).

The biocide containing liquid is preferably an aqueous solution, suspension or emulsion of the biocide.

The biocide preferably comprises hydrogen peroxide ($H_2O_2$) in combination with a catalyst for enhancing the activity thereof, the catalyst preferably comprising a superoxidedismutase formed from the combination of elemental copper (Cu), silver (Ag), manganese (Mn) and zinc (Zn).

The $H_2O_2$ is typically present in the biocide in an amount of about 0.000003% to about 15% v/v, preferably about 0.003% to about 3% v/v, in particular about 0.3% v/v.

The Cu, Mn and Zn are typically present in an amount of about 100 ppb to about 1000 ppm, preferably about 3 to 7 ppm, in particular about 5 ppm.

The Ag is typically present in an amount of about 100 ppb to about 1000 ppm, preferably about 3 to 9 ppm, in particular about 7 ppm.

The liquid biocide is preferably provided in the form of a fine spray or mist.

The method is preferably used to purify the air in an air conditioning unit of a building such as an office block, house, hospital, shopping mall, stadium, or the like, a vehicle such as a motor vehicle, bus, truck, ship or train, an aircraft or the like, in mines and other underground environments or an exhaust gas or other gas emission from an industrial factory or the like.

The invention extends to a system for purifying a gas stream or gaseous body, the system including a gas purifying unit arranged to bring a liquid biocide into contact with a gas stream or gaseous body passing through the unit in order to eliminate, in whole or in part, contaminants in the gas stream or gaseous body.

The method and system find particular application in the elimination of contaminants selected from inorganic contaminants such as CO, $NO_2$ and $SO_2$, organic contaminants such as formaldehyde, hexane and acetone, particulate matter such as dust particles and smoke particles, and microorganisms such as viruses for example influenza, small pox and the like, bacteria, for example *legionella* and other airborne bacteria, and fungi or their spores, in particular anaerobic microorganisms.

The method and system are preferably used in the combating of sick building syndrome (SBI) and building related illness (BRI).

An embodiment of the invention is described in detail in the following passages of the specification which refer to the accompanying drawings. The drawings, however, are merely illustrative of how the invention might be put into effect, so that the specific form and arrangement of the features shown is not to be understood as limiting on the invention.

BRIEF DESCRIPTION OF THE DRAWINGS

The invention will now be described in more detail, by way of example only, with reference to the accompany drawings in which.

DETAILED DESCRIPTION OF PREFERRED EMBODIMENTS

The invention provides a method and system for eliminating, in whole or in part, contaminants in a gas stream or gaseous body such as air or an exhaust gas or gas emission stream.

Figure 1:
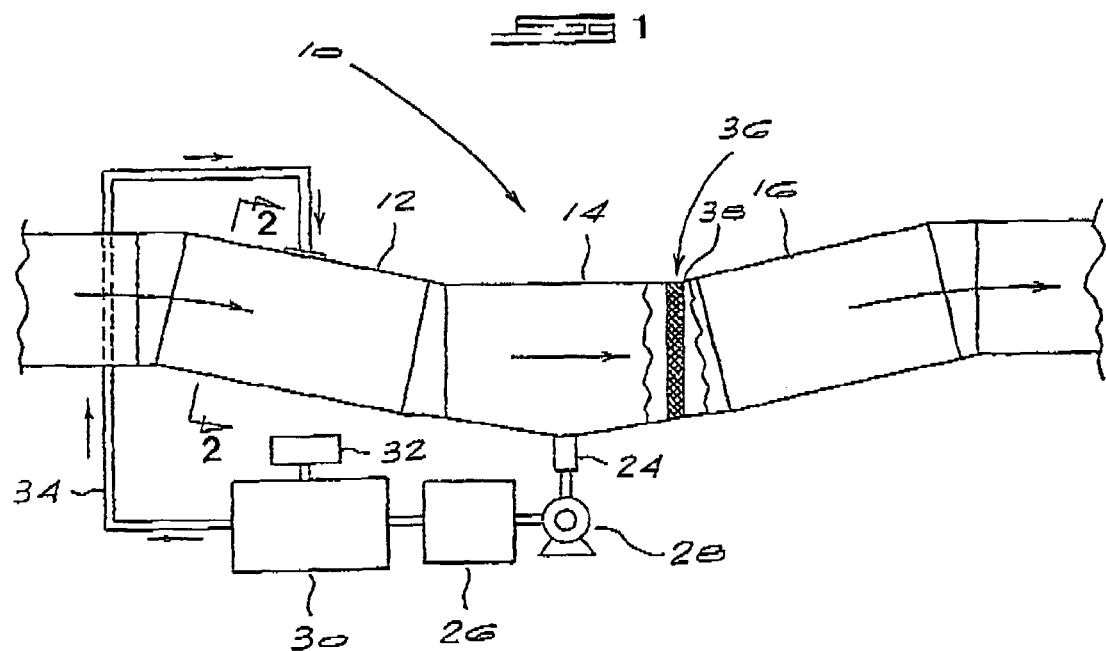
FIG. 1 is a schematic side view of a gas purification system of the invention.
Figure 2:
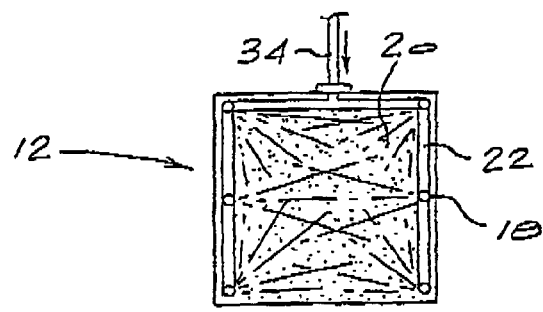
FIG. 2 is a cross-sectional view on the line 2—2 of FIG. 1.

Referring to FIG. 1 of the drawings, a gas purification system 10 of the invention is shown schematically. The system 10 consists of a scrubber unit 12, as shown more clearly in FIG. 2, a liquid collection unit 14 and an air dryer unit 16 (optional), all in gas flow communication with one another.

The scrubber unit 12 includes a plurality of spray nozzles 18 for introducing a fine spray or mist 20 of a biocide solution, suspension or emulsion into the scrubber chamber 22 thereof. As air or other gas containing contaminants passes through the scrubber 12, in the direction of the arrows in FIG. 1, it contacts the spray or mist. As the contaminants in the gas or air stream come into contact with the fine mist or spray, they are taken up by the spray or mist droplets and hence removed from the air stream. In addition, the biocide acts to kill the micro-organisms. The biocide solution, typically including water as the carrier, collects under normal gravitational forces in the collection unit 14 whereafter it flows through outlet conduit 24 and is pumped into a filter unit 26 by a pump 28. The contaminants in the solution are removed in the filter 26 whereafter the water is pumped into the water feed tank 30. A biocide feeder 32, typically in the form of a drip supply tank, feeds biocide into the water in the tank 30 before it is pumped via the conduit 34 into the scrubber unit 12. The collection unit 14 includes a water separator 36 at a front end 38 thereof for separating excess water droplets as the air stream exits the collection unit 14. The decontaminated air passing from the collection unit 14 may have a relatively high relative humidity, in which case it is optional to pass it through a heating chamber or dryer unit 16 before continuing through the rest of the air conditioning system.

It is envisaged that the method and system of the invention can be used to eliminate, in whole or in part, a number of contaminants including inorganic contaminants such as CO, $NO_2$ and $SO_2$, organic contaminants such as formaldehyde, hexane and acetone, particulate matter such as dust particles and smoke particles, and microorganisms such as viruses for example influenza, small pox and the like, bacteria, for example *legionella* and other airborne bacteria, and fungi or their spores, in particular anaerobic micro-organisms. The combination of biocide, which acts on the micro-organisms, and the fine spray, which acts to remove particles out of the air, are believed to provide an effective air or gas purification method and system.

In order to evaluate the efficacy of the system and method of the invention, the applicant retained the services of an independent, fully accredited testing company (Environmental Science Service Consultants ESSC) to conduct tests on air containing a number of different contaminants. In terms of the methodology, the following pollutants were introduced into the air.

Inorganic gasses: CO, $NO_2$, $SO_2$;

Organic gasses: formaldehyde, hexane and acetone;

Particulate matter: dust of various particle sizes and tobacco smoke; and

Micro-organisms.

The tests were carried out using a prototype which was built as a self-contained, re-circulatory unit housing +/−12 $m^3$ of air volume. Airflow through the prototype was maintained at +/−0.5 $m^3/s$ at a speed of +/−2 m/s, producing a 6 second air change. This allowed for the production of a ten air change cycle every minute, forming a 1 minute=1 hour ratio. Thus, for every minute that the unit circulated the air, it was equivalent to 1 hour in real time. Hence, 24 minute exposure time equates into one day or a 24 hour period.

The results of the tests are set out below.

TABLE 1

Inorganic contaminants elimination per 24 hour period

| CONTAMINANT | PERCENTAGE ELIMINATION |
|---|---|
| Sulphur dioxide ($SO_2$) | 58% |
| Carbon monoxide (CO) | 76% |

TABLE 1-continued

Inorganic contaminants elimination per 24 hour period

| CONTAMINANT | PERCENTAGE ELIMINATION |
|---|---|
| Oxygen ($O_2$) | 0.5% increase |
| Nitrogen dioxide ($NO_2$) | 91% elimination |
| Carbon dioxide ($CO_2$) | Pending |

TABLE 2

Organic contaminants elimination per 5 hour cycle

| CONTAMINANT | PRE-TEST (ppm) | POST-TEST (ppm) | RE-DUCTION (ppm) | PERCENTAGE ELIMINATION |
|---|---|---|---|---|
| Formaldehyde | — | — | — | Pending |
| Hexane | 1825.6 | 1125 | −700.6 | 38.3% |
| Acetone | 2941.2 | 366 | −2904.6 | 98.75% |

TABLE 3

Particulate material

| CONTAMINANT | PERCENTAGE ELIMINATION |
|---|---|
| Fine dust particles | 99.9% |
| Coarse dust particles | 99.9% |

In addition to the above contaminants, bacterial microbes from toilet water of various contamination degrees were brought into contact with the biocide solution in one passage of airflow through the system and a 99.9% elimination was obtained.

In the light of the above test results, it is believed that the method and system of the invention are capable of eliminating, at least in part, micro-organisms and harmful gasses that cause sick building syndrome and related illness. The system is relatively inexpensive to manufacture and the chemical compounds for the biocide are readily available and cost effective. The chemicals used are human-safe, non-toxic and provided in quantities which are well below OSHA regulations.

The invention claimed is:

1. A method of purifying or cleansing a stream of gas or a gaseous body containing one or more contaminants, comprising the steps of contacting the gas stream or gaseous body with a biocide containing liquid so as to eliminate, in whole or in part, the contaminant(s) wherein the biocide comprises hydrogen peroxide ($H_2O_2$) in combination with a catalyst for enhancing the activity thereof and the catalyst comprises a superoxidedismutase formed from the combination of elemental copper (Cu), silver (Ag), manganese (Mn) and zinc (Zn).

2. A method according to claim 1, wherein the stream of gas is an air stream or an exhaust gas stream.

3. A method according to claim 1, wherein the biocide containing liquid is an aqueous solution, suspension or emulsion of the biocide.

4. A method according to claim 1, wherein the biocide comprises about 0.000003% to about 15% v/v $H_2O_2$, and about 100 ppb to about 1000 ppm each of Cu, Mn, Zn and Ag.

5. A method according to claim 4, wherein the biocide comprises about 0.003% to about 3% v/v $H_2O_2$, about 3 to 7 ppm each of Cu, Mn and Zn, and about 3 to 9 ppm Ag.

6. A method according to claim 5, wherein the biocide comprises about 3% v/v $H_2O_2$, about 5 ppm each of Cu, Mn and Zn, and about 7 ppm Ag.

7. A method according to claim 1, wherein the liquid biocide is provided in the form of a fine mist or spray.

8. A method according to claim 1, wherein the method is used to purify the air in an air conditioning unit of a building, vehicle, an aircraft, in mines, and other underground environments or an exhaust gas or other gas emission from an industrial factory.

9. A method according to claim 1, wherein the contaminants are selected from the group consisting of inorganic contaminants, organic contaminants, particulate matter and microorganisms.

10. A method according to claim 7, wherein the contaminants are selected from the group consisting of CO, $NO_2$, $SO_2$, formaldehyde, hexane, acetone, dust particles, smoke particles, viruses, bacteria, and fungi or their spores.

11. A method according to claim 1 for use in combating sick building syndrome or building related illness.

* * * * *